(12) United States Patent
Nino et al.

(10) Patent No.: US 10,219,853 B2
(45) Date of Patent: *Mar. 5, 2019

(54) ROBUST NOSE TORQUE-LIMITING DEVICE

(71) Applicant: ECA Medical Instruments, Newbury Park, CA (US)

(72) Inventors: John Nino, Simi Valley, CA (US); David Ivinson, Camarillo, CA (US)

(73) Assignee: ECA Medical Instruments, Thousand Oaks, CA (US)

( * ) Notice: Subject to any disclaimer, the term of this patent is extended or adjusted under 35 U.S.C. 154(b) by 504 days.

This patent is subject to a terminal disclaimer.

(21) Appl. No.: 14/856,369

(22) Filed: Sep. 16, 2015

(65) Prior Publication Data

US 2016/0030101 A1 Feb. 4, 2016

Related U.S. Application Data

(63) Continuation of application No. 13/191,203, filed on Jul. 26, 2011, now Pat. No. 9,162,350.

(Continued)

(51) Int. Cl.
*A61B 17/88* (2006.01)
*B25B 23/14* (2006.01)
(Continued)

(52) U.S. Cl.
CPC .......... *A61B 17/8875* (2013.01); *A61B 90/03* (2016.02); *B25B 15/04* (2013.01);
(Continued)

(58) Field of Classification Search
CPC ............... A61B 17/8875; A61B 90/03; A61B 2090/031; B25B 15/04; B25B 23/141; B25B 23/142; B25B 23/1427
(Continued)

(56) References Cited

U.S. PATENT DOCUMENTS 975,285 A 11/1910 Robertson et al.
3,283,638 A 11/1966 Ansingh
(Continued)

FOREIGN PATENT DOCUMENTS

WO WO 1992/003262 A1 3/1992
WO WO 2001/070465 A1 9/2001
WO WO 2005/077603 A1 8/2005

OTHER PUBLICATIONS

Holmed Corporation Surgical Instruments Catalog, www.holmed.net, 40 Norfolk Avenue, South Easton, MA, USA, 02375.
(Continued)

*Primary Examiner* — Hadi Shakeri
(74) *Attorney, Agent, or Firm* — Baker & Hostetler LLP; Mark H. Krietzman

(57) ABSTRACT

A torque-limiting driver has a handle, a body, a torque-limiting assembly and a work-piece engaging tip. The torque-limiting assembly includes an upper and lower shank that have a plurality of teeth circumferentially spaced. The teeth have a vertical face, an inclined face, and a flat peak. There is a spring for applying pressure across the upper and lower shank with multiple washers interposed between the lower shaft and spring. In some instances, there is a round square drive with arched catches having preselected radii to assure operation over certain cycles at selected torque and to reduced nose cone damage and breakage at a predetermined inch pounds of torque.

10 Claims, 13 Drawing Sheets

Related U.S. Application Data

(60) Provisional application No. 61/463,548, filed on Feb. 19, 2011, provisional application No. 61/368,519, filed on Jul. 28, 2010.

(51) Int. Cl.
*B25B 23/142* (2006.01)
*B25B 15/04* (2006.01)
*A61B 90/00* (2016.01)

(52) U.S. Cl.
CPC .......... *B25B 23/141* (2013.01); *B25B 23/142* (2013.01); *B25B 23/1427* (2013.01); *A61B 2090/031* (2016.02)

(58) Field of Classification Search
USPC .......................................... 81/473
See application file for complete search history.

(56) References Cited

U.S. PATENT DOCUMENTS

| | | | |
|---|---|---|---|
| 3,695,059 A | 10/1972 | Laubach | |
| 3,728,892 A | 4/1973 | Sangster | |
| 4,883,130 A | 11/1989 | Dixon | |
| 5,020,954 A | 6/1991 | Dreger | |
| 5,152,631 A | 10/1992 | Bauer | |
| 6,128,984 A | 10/2000 | Haupt | |
| 7,197,968 B2 | 4/2007 | Bubel | |
| D543,433 S | 5/2007 | Gao | |
| 7,243,581 B1 | 7/2007 | Gao | |
| 7,272,999 B2 * | 9/2007 | Cutler | B25B 15/02 81/467 |
| D557,584 S | 12/2007 | Gao | |
| D562,665 S | 2/2008 | Gao | |
| 7,334,509 B1 | 2/2008 | Gao | |
| 7,389,700 B2 | 6/2008 | Gao | |
| 7,395,738 B1 | 7/2008 | Nelson | |
| 7,434,623 B2 | 10/2008 | Von Gynz-Rekowski | |
| D580,730 S | 11/2008 | Gao | |
| 7,467,576 B2 | 12/2008 | Gao | |
| 7,516,676 B2 | 4/2009 | Gao | |
| 7,584,936 B2 | 9/2009 | Lewis et al. | |
| 7,740,249 B1 | 6/2010 | Gao | |
| 7,762,164 B2 | 7/2010 | Nino et al. | |
| 7,793,573 B2 * | 9/2010 | Gao | B25B 15/02 81/475 |
| 7,806,027 B1 | 10/2010 | Gao | |
| 7,810,817 B1 | 10/2010 | Gao | |
| 8,418,587 B2 | 4/2013 | DeBaker | |
| 8,851,201 B2 | 10/2014 | Limberg et al. | |
| 9,162,350 B2 | 10/2015 | Nino et al. | |
| 9,877,764 B2 * | 1/2018 | Nino | B25B 15/04 |
| 2005/0187549 A1 | 8/2005 | Jackson | |
| 2006/0016300 A1 | 1/2006 | Bubel | |
| 2006/0278051 A1 | 12/2006 | Gauthier et al. | |
| 2009/0293687 A1 * | 12/2009 | Nino | B25B 15/02 81/476 |
| 2010/0192736 A1 | 8/2010 | Burch et al. | |
| 2010/0275738 A1 * | 11/2010 | Taylor, Jr. | B25B 13/06 81/121.1 |
| 2010/0307299 A1 | 12/2010 | Nino et al. | |
| 2014/0260825 A1 * | 9/2014 | Milligan | B25B 13/06 81/124.6 |

OTHER PUBLICATIONS

Beere Medical Line of Custom Configured Ortho-Grip Handles; www.teleflexmedicaloem.com.
Bradshaw Medical, Inc., Non-Ratcheting and Fixed Comfort Grip Handles; www.bradshaw-medical.com/nrds.html.
Paragon Medical Standard Surgical Instrumentation Catalog; www.paragonmedical.com/catalog/complete-catalog.html.
Quick Connectors, Gauthier Biomedical, Inc.; www.gauthierbiomedical.com/products/quick-connectors/.
Silicone Handles, Gauthier Biomedical, Inc.; www.gauthierbiomedical.com/products/silicone-handles.
Ratcheting Screwdrivers, Gauthier Biomedical, Inc.; www.gauthierbiomedical.com/products/products.
Torque Instruments, Gauthier Biomedical, Inc.; www.gauthierbiomedical.com/products/torque-instruments/.
Symmetry Medical Inc.; Radel R Instrument Handles, Silicone Instrument Handles, Ratcheting Screwdriver Handles, and Spinal Instruments; www.symmetrymedical.com.
International Patent Application No. PCT/US2012/025514; Int'l Preliminary Report on Patentability; dated Aug. 21, 2013; 6 pages.
European Patent Application No. 12747647.1; Extended Search Report; dated Sep. 19, 2017; 8 pages.

\* cited by examiner

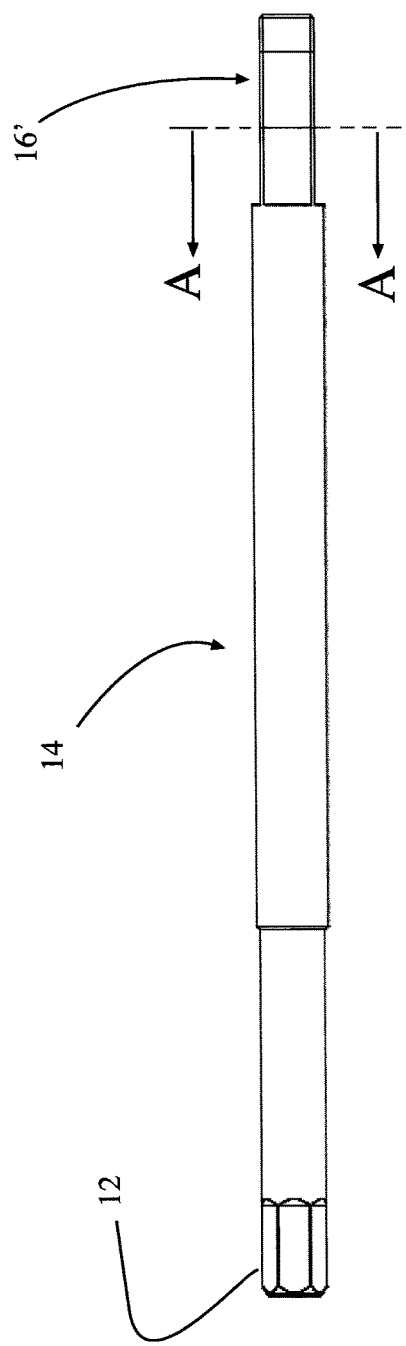
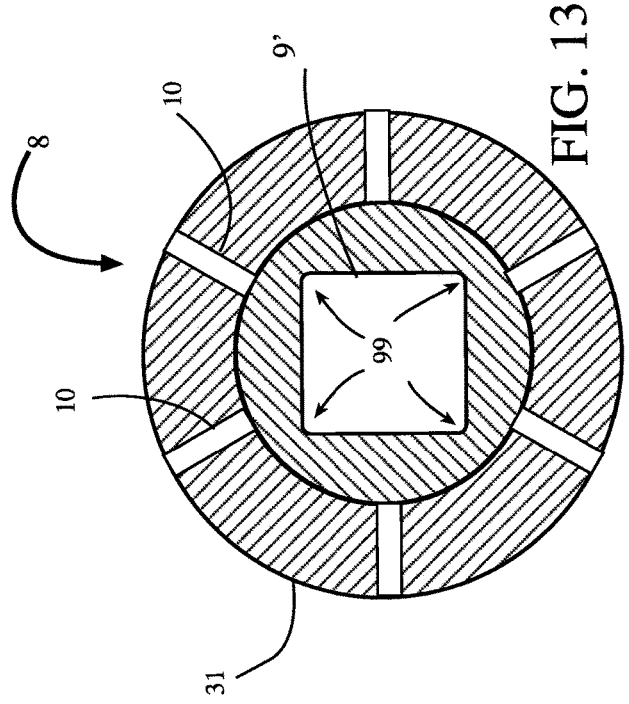

With One Staineless Steal Washer

With Two Staineless Steal Washers

ROBUST NOSE TORQUE-LIMITING DEVICE

RELATED APPLICATION

This application is a continuation of U.S. patent application Ser. No. 13/191,203, filed Jul. 26, 2011, and claims the benefit of and priority to U.S. Provisional Applications Ser. No. 61/463,548 with a filing date of Feb. 19, 2011 and 61/368,519 with a filing date of Jul. 28, 2010, all of which are incorporated as if fully set forth herein in their entirety.

BACKGROUND

1. Field

This disclosure relates to a medical use driver tool and, in particular, to a torque-limiting driver that disengages at a predefined torque limit.

2. General Background

Torque-limiting drivers are widely used throughout the medical industry. These torque-limiting drivers have a factory pre-set torque to ensure the accuracy and toughness required to meet a demanding surgical environment.

The medical industry has made use of both reusable and disposable torque-limiting drivers. In a surgical context, there is little room for error and these drivers must impart a precise amount of torque.

Reusable drivers require constant recalibration to ensure that the driver is imparting the precise amount of torque. Recalibration is a cumbersome task but must be done routinely.

Disposable drivers are an easy to use and reliable alternative to the reusable drivers. Typically, a medical device such as an implant, for example, is packaged with a disposable driver designed to the implant's specifications. Once the driver has been used, it can be discarded. Thus, a surgeon can have complete confidence that the disposable driver, packaged with an implant, will impart the precise amount of torque. Typically, the torque requirement is different for different operations and for different implants. For example, applications may include those in the field of orthopedic surgery, construction and emplacement of implants, etc.

These disposable drivers have been used for low torque applications. The standard torque values in these applications typically range from 4 to 20 inch-ounces. It has, however, been a challenge to develop a reliable disposable driver capable of imparting higher torques for larger applications.

Disclosure

Torque is a measure of how much force acting on an object causes that object to rotate. In the case of a driver and a fastener, this measurement can be calculated mathematically in terms of the cross product of specific vectors:

$$\tau = r \times F$$

Where r is the vector representing the distance and direction from an axis of a fastener to a point where the force is applied and F is the force vector acting on the driver.

Torque has dimensions of force times distance and the SI unit of torque is the Newton meter (Nm). The joule, which is the SI unit for energy or work, is also defined as an Nm, but this unit is not used for torque. Since energy can be thought of as the result of force times distance, energy is always a scalar whereas torque is force cross-distance and so is a vector-valued quantity. Other non-SI units of torque include pound-force-feet, foot-pounds-force, ounce-force-inches, meter-kilograms-force, inch-ounces or inch pounds.

A disposable torque-limiting driver, in accordance with the present disclosure, has a handle, a cylindrical body and a work-piece engaging tip. Within the cylindrical body there is a torque-limiting assembly. The torque-limiting assembly includes an upper cylindrical shank and a lower cylindrical shank. The upper cylindrical shank and the lower cylindrical shank have a plurality of teeth. The teeth have a vertical face, an inclined face and a substantially flat peak. The inclined face is defined by a first radius of curvature that transitions to the substantially flat peak. The teeth are spaced circumferentially and spiral around the upper cylindrical shank and a lower cylindrical shank. There is a spring for applying pressure across the upper cylindrical shank and the lower cylindrical shank. The teeth of the upper cylindrical shank and the lower cylindrical shank engage for relative rotation when the handle is turned and disengage when a predetermined value of torque is exceeded.

Smooth repeat operation is encouraged with specific dual bearing surfaces.

A round square implementation provides a range of use over predetermined cycles of up to almost 150 inch pounds rotations without cracking the plastic nose cone. In some instances a square engagement with radiuses corners having radii between about 0.1482 and about 0.1638 inches are optimal. In some instances a square engagement with radiuses corners having radii between about 0.1292304 and about 0.1716 inches are optimal. In other instances a square engagement with radiuses corners having radii is between about 0.1266 and about 0.1794 inches is optimal.

A torque driver capable of transferring high torque with a spring having a spring constant (also referred to as a force constant) which exerts a greater force in an initial (rest) state via a multiple washer bearing interface. A single washer interface with end of spring may have a tendency to grip or bind spring and washer; a multiple washer interface provides a bearing surface between spring and remote second washer. Elimination or reduction of binding or gripping between washer and spring may provide a smoother rotation.

DRAWINGS

FIG. 11 is shaft in accordance with the present disclosure.

FIG. 12 is a cross sectional view at line A-A of FIG. 11 in accordance with the present disclosure.

FIG. 13 is a front view of the nose of FIG. 10 in accordance with the present disclosure.

Figure 1:
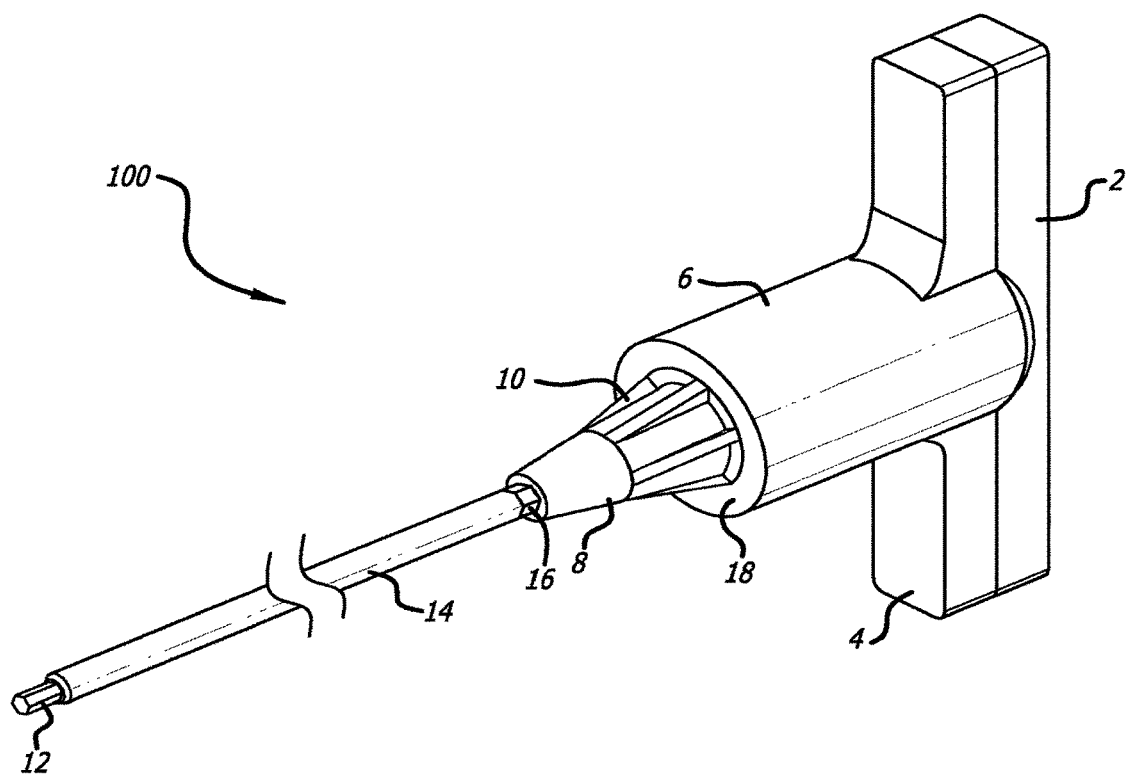
FIG. 1 is a perspective view of a driver in accordance with the present disclosure.

While the specification concludes with claims defining the features of the present disclosure that are regarded as novel, it is believed that the present disclosure's teachings will be better understood from a consideration of the following description in conjunction with the appendices, figures, in which like reference numerals are carried forward. All descriptions and callouts in the Figures and Appendices are hereby incorporated by this reference as if fully set forth herein.

Further Disclosure

Referring to FIGS. 1-9, there is a torque-limiting driver 100. The torque-limiting driver 100 has a generally T-shaped handle. The T-shaped handle includes arms 4 at one end an axially extending generally hollow cylindrical body 6, a cap 2 that covers the same end of the T-shaped handle and a cylindrical end 18 opposite the T-shaped handle on the cylindrical body 6. The cap 2 may be snap-fitted to the cylindrical body 6, or may be welded, or attached by any equivalent thereof and the body is preferably molded from a plastic or other economical equivalents.

At the cylindrical end 18, there is a lower shank 700 that has and annularly tapering body and a nose cone 8 along its length. The lower shank 700 may have a plurality of support flanges 10 that add strength while saving material. At one end, the lower shank 700 tapers to a drive socket 9 at the end of the nose cone 8 molded to engage a shaft 14. The shaft 14 maybe substantially linear with a proximal end that mates with said drive socket. The shaft 14 may be hexagonal or cylindrical in transverse cross-sectional shape and is provided, at one end, with a work piece-engaging distal tip 12, adapted for engagement with an associated work-piece, such as a fastener or the like. The work piece-engaging distal tip 12 is shown to be a hex wrench, but could be a screwdriver, wrench, or any other tool or medical tool arrangement. At an opposite end, the lower shank 700 has a plurality of teeth 82 arranged in a crown gear formation, a circumferential rim 31 extending radially outwardly and an internally threaded axial bore.

Figure 2:
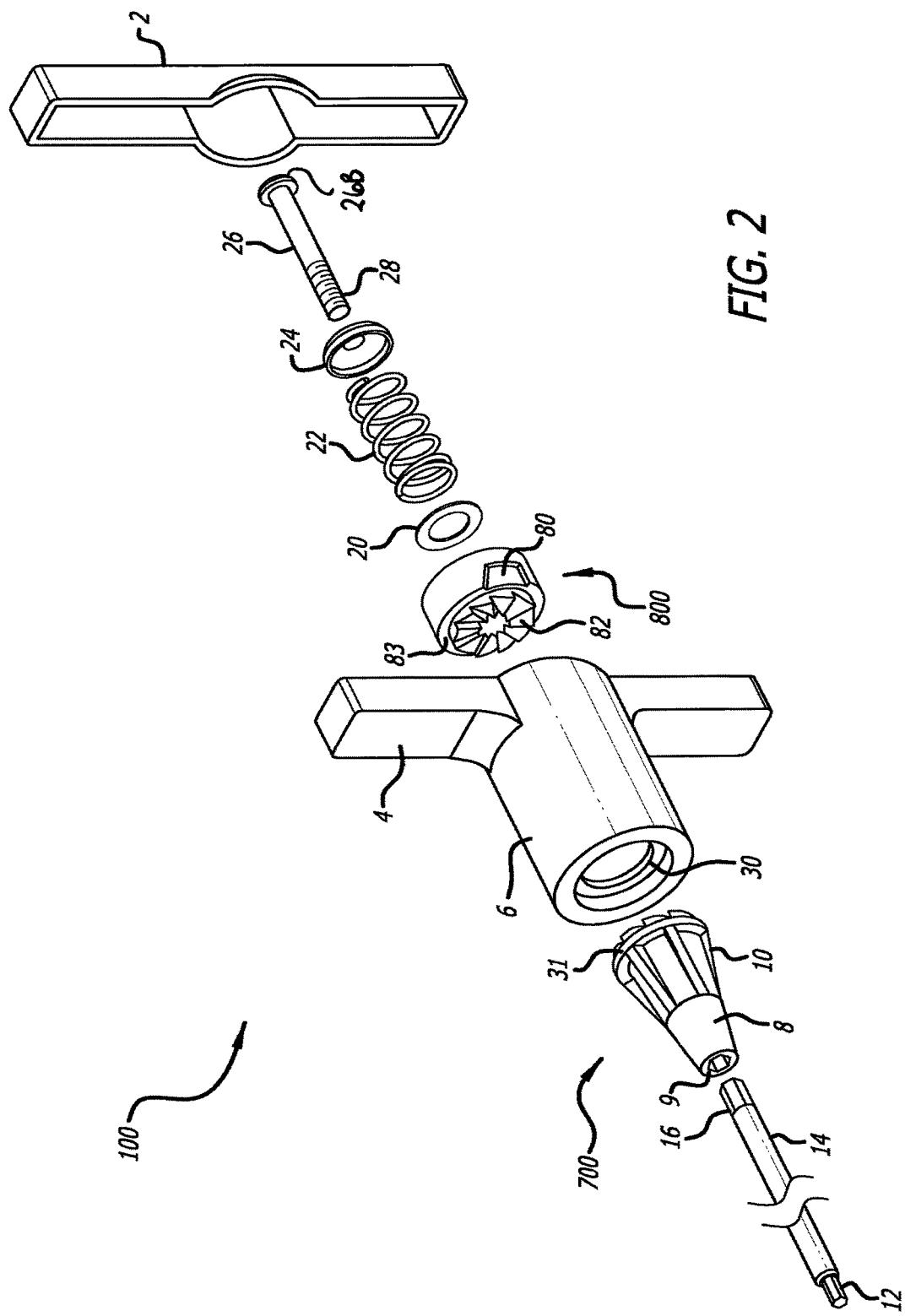
FIG. 2 is an exploded view of a driver in accordance with the present disclosure.

FIG. 2 is an exploded view of the driver 100. Inside the cylindrical body 6 a clutch assembly is disposed. The clutch assembly includes an upper shank 800 for forcibly engaging the lower shank 700. The upper shank 800 has a bottom face that has teeth 82 arranged in a crown gear formation and an annular flange or circumferential rim 83 extending radially outwardly. Shown on FIG. 5, the upper shank 800 includes an annular body or outer cylindrical shank 84, an axial bore 92 through an inner shank 86. The inner shank 86 and outer shank 84 are connected via inner supports 88, leaving the upper shank 800 substantially hollow with internal spaces 90 on a top face.

The upper shank 800 also includes at least one recess 80 on the side of the outer shank. The recess 80 is provided as a cylindrical cut, relief or recess into the side of the outer shank and maybe provided as a square or rectangular cut or the cut may have a slanted side or sides relative to the axis of the upper shank 800 as shown in FIG. 2.

In assembly, the shaft 14 at its proximal end forms drive connection 16 which is received into the drive socket 9 of the lower shank 700. A washer (not detailed in the implementation) may be provided between the circumferential rim 31 of the lower shank 700 and a circumferential flange 30 extending radially inward within the hollow of the cylindrical body 6. Alternatively, the circumferential rim 31 of the lower shank 700 may be provided flush against circumferential flange 30 of the cylindrical body 6.

Drive socket 9 and the connection 16 are shown having corresponding cross sectional shape. In this implementation the hexagonal shape provides multiple stops and surface area to facilitate consistent operation over the anticipated use profile without significant wiggle or loosening of the shaft 14 from the drive socket 9. A use profile includes, but is not limited to, such factors as required lbf (load) or inch pounds of torque, number of uses, cycle time, material nose cone 8 is formed of and material forming shaft 14.

The opposite side of the circumferential flange 30 receives the circumferential rim 83 of the upper shank 800 allowing the teeth 82 of the lower shank 700 to engage the teeth 82 of the upper shank 800 when a torque is applied.

Figure 3:
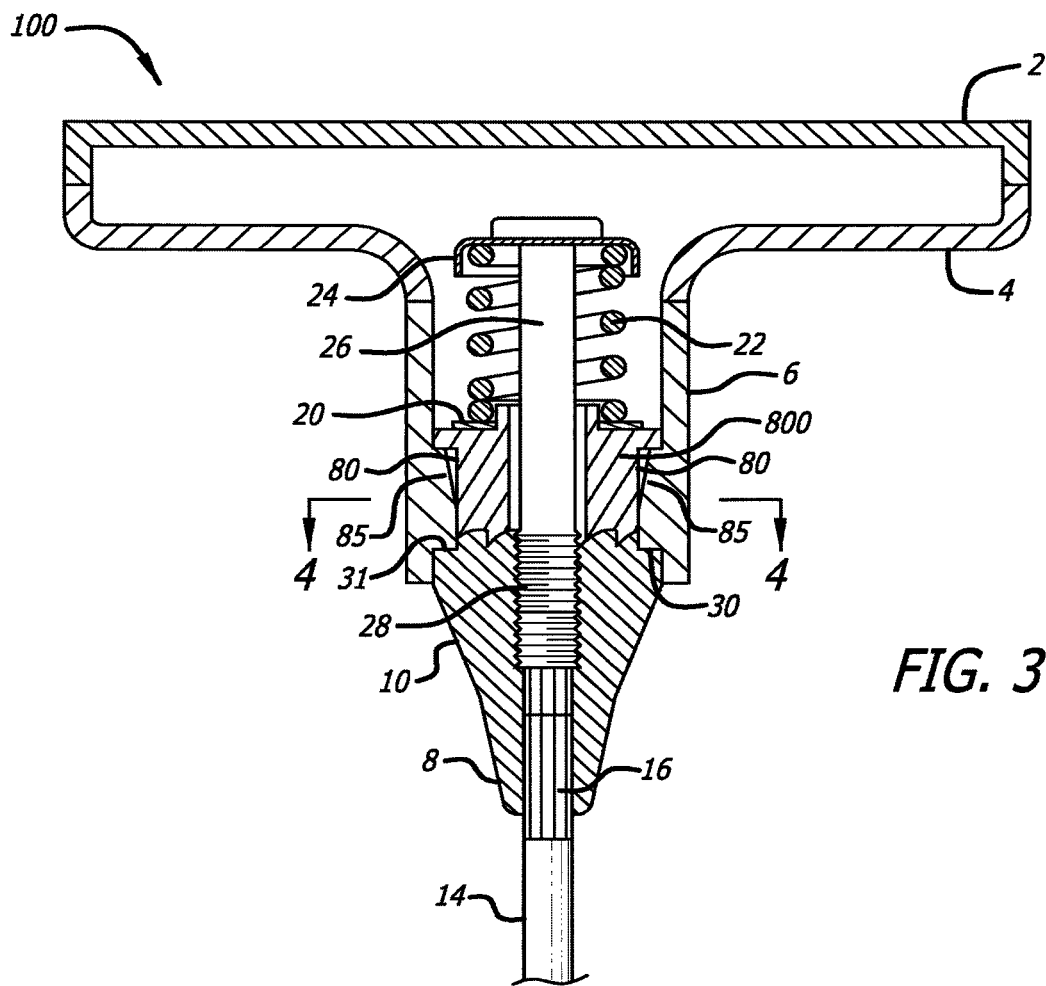
FIG. 3 is a vertical cross sectional view of a driver in accordance with the present disclosure.
Figure 4:
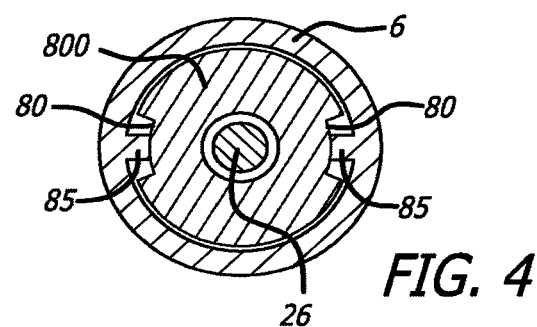
FIG. 4 is a horizontal cross sectional view of a driver in accordance with the present disclosure.
Figure 5:
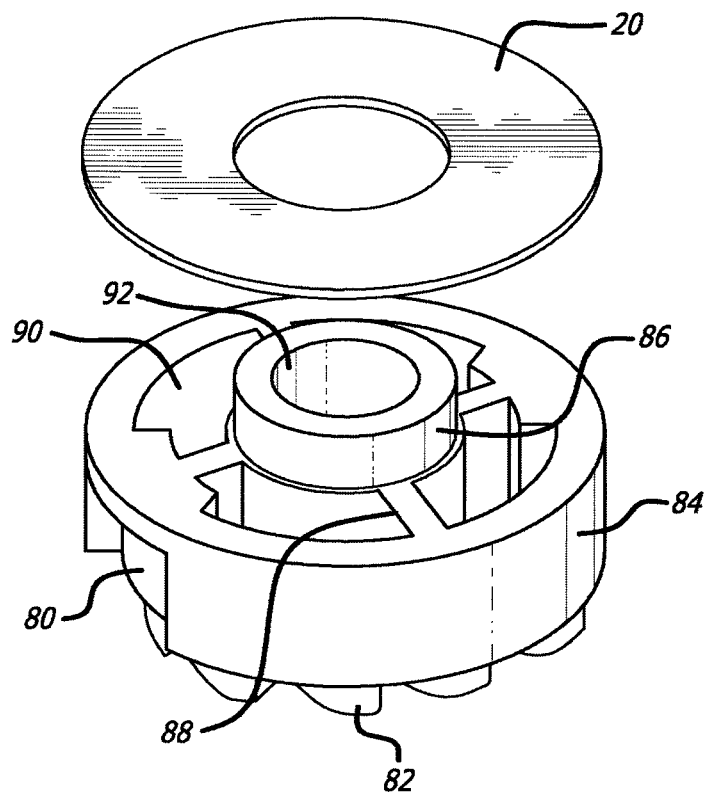
FIG. 5 is a perspective view of an upper shank in accordance with the present disclosure.

Integrally formed within the cylindrical body 6, a protrusion 85 mates with the recess 80 of the upper shank 800. FIG. 3 and FIG. 4 are cross sectional views that best illustrate the protrusion 85 in relation with the recess 80. The protrusion 85 extends inward in a radial fashion and has a length along the axis of the cylindrical body 6 for relative moveable engagement within the recess 80. This engagement provides a locking mechanism of the shaft 14 relative to the T-shaped handle via the upper shank when pressure is applied across the lower shank 700 and the upper shank 80. The recess 80 is provided circumferentially wider than the protrusion 85 for allowing the cylindrical body 6 and the T-shaped handle to rotate in reverse a predetermined distance from a locked position without subsequent reverse rotation of the work piece-engaging tip 12. Thus, the at least one recess 80 and at least one protrusion 85 lock the T-shaped in one direction providing the necessary torque to drive a fastener and allow for a predetermined amount of reverse rotation before unscrewing the fastener.

Force is applied across the lower shank 700 and the upper shank 800 via a spring 22 within the cylindrical body 6. Inside the cylindrical body 6, shown in FIG. 2 and FIG. 5, a washer 20 is provided between the upper shank 800 and the spring 22. The washer transfers pressure from the spring 22 over the top face of the upper shank 800. At an end of the spring 22 opposite the upper shank 800, a cup washer 24 and a locking fastener 26 hold the spring 22 in a compressed state. The locking fastener 26A has a fastener head 26B and has a threading 28 that engages a complementary threading within an axial bore 72 of the lower shank 700. Thus, imparting pressure between the respective teeth 82 of the lower shank 700 and the upper shank 800. The spring 22 and the locking fastener 26A provide the proper tensioning and biasing for the clutch assembly and, generally, the locking fastener 26A is adjustable to provide proper tension and calibration.

Figure 6:
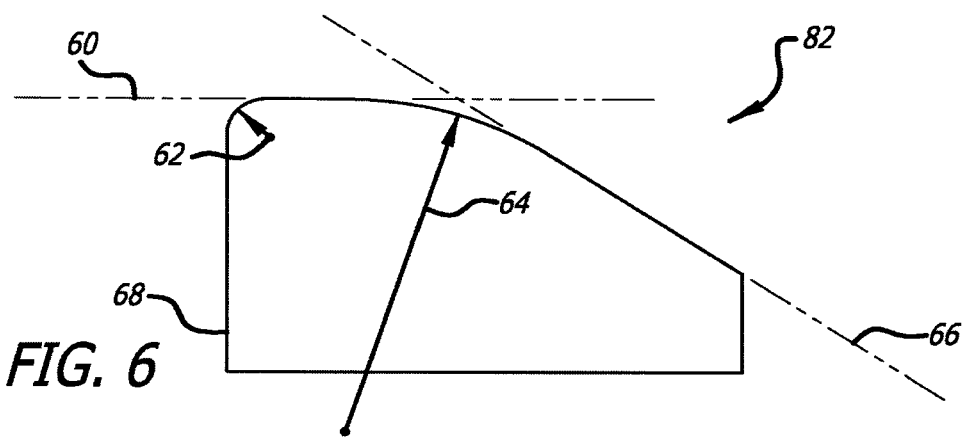
FIG. 6 is a profile of a tooth from a clutch assembly in accordance with the present disclosure.
Figure 7:
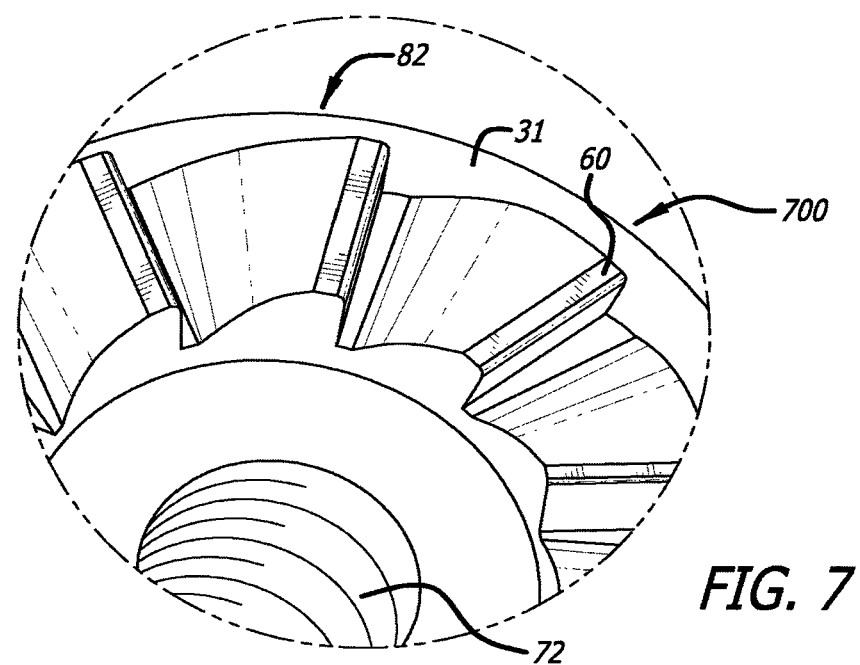
FIG. 7 is a perspective view of the teeth from a clutch assembly in accordance with the present disclosure.
Figure 8:
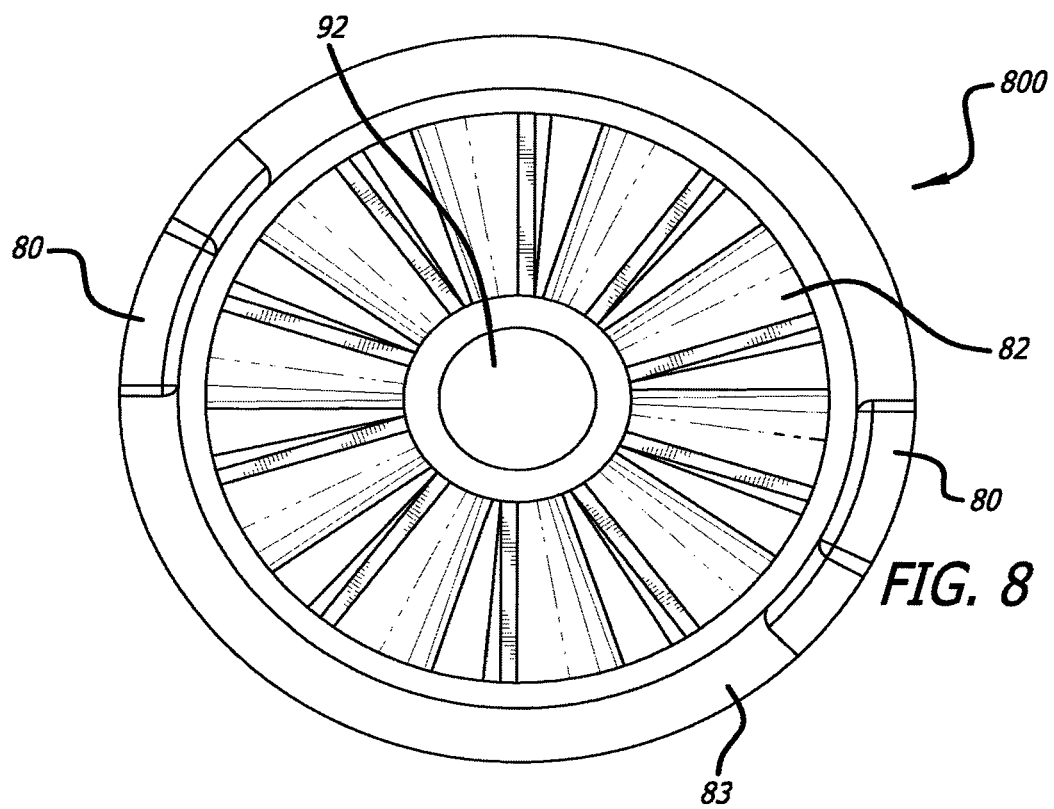
FIG. 8 is a top view of the teeth from a clutch assembly in accordance with the present disclosure.
Figure 9:
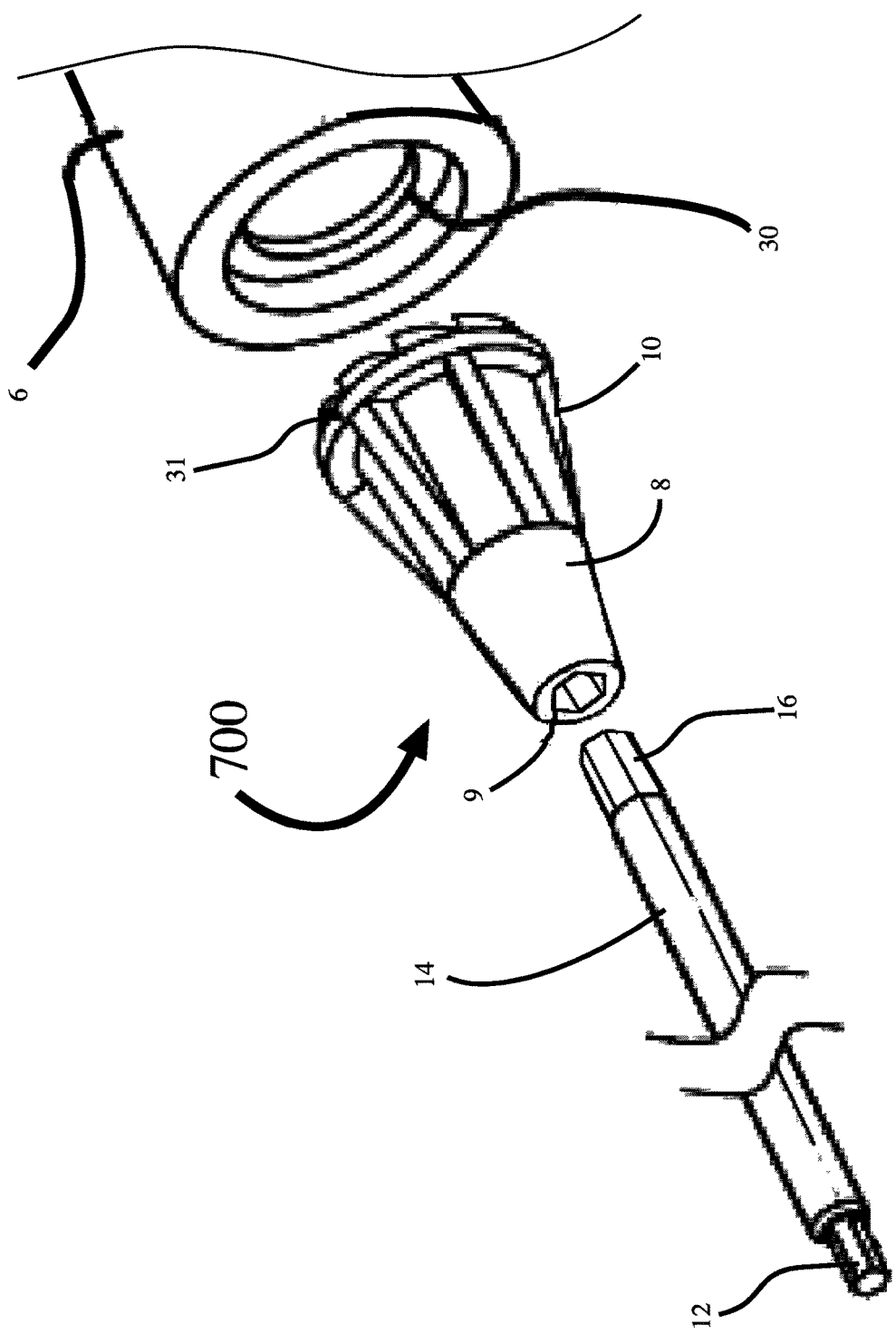
FIG. 9 is a partial exploded view of the nose region of FIG. 2.

Formed on the top face of the lower shank 700 and the bottom face of the upper shank 800 are the plurality of teeth 82 that forcibly engage to impart torque from the T-shaped handle to the work piece when a torque is applied. Referring to FIGS. 6-7, tooth 82 has an inclined face 66 that smoothly transitions to a substantially flat peak 60, via a first radius of curvature 64. The substantially flat peak 60 subsequently transitions smoothly, via a second radius of curvature, to a vertical face 68 that is substantially parallel to the axis of the lower shank 700 and the upper shank 800. The first radius of curvature is typically much larger than the second radius of curvature.

Experimental results have shown that a tooth having an inclined face that smoothly transitions to a substantially flat face is capable of imparting a substantial increase in torque to a fastener. In one experiment, a ten-fold increase in torque was observed. This increase in torque is due to the frictional forces associated with the smoothly transitioning curve of an inclined face 66 of the teeth 82.

In a simplified example, when two uniform inclines are frictionally engaged, only one static force, having a single coefficient of static force, is acting against the relative movement of the two inclines. However, when the two inclines are not uniform, more than one coefficient of static force can be observed, thus resulting in a higher disinclination to movement.

The teeth 82 are circumferentially spaced in a crown gear formation of the top face and bottom face of the lower shank 700 and the upper shank 800 respectively. The teeth 82 are also preferably configured in a spiral formation, best shown in FIG. 7. Each face of the lower shank 700 and the upper shank 800 has an inner radius and an outer radius and the teeth 82 spiral around the inner radius resulting in a larger tooth detail when viewing the tooth from the outer radius relative to the tooth detail when viewing the tooth from the inner radius. The spiral configuration of the teeth 82 can also be defined as having a longer inclined face 66 at the edge of the tooth on or near the outer radius relative to the inclined face 66 at the edge of the tooth on or near the inner radius of the lower shank 700 and the upper shank 800. Results have shown that teeth arranged in a spiral configuration provide an increased reliability and precision in torque consistency when compared to their non-spiral counterparts.

The substantially flat peak 60 of the teeth 82 can be as wide at the inner radius as they are at the outer radius. Alternatively, the substantially flat peak 60 may be wider at the outer radius and taper toward the inner radius.

The vertical faces 68 of the teeth 82 of the lower shank 700 and the upper shank 800 respectively engage when a torque is applied to prevent relative rotation of the lower shank 700 and the upper shank 800 in one direction. The inclined faces 66 engage to accommodate relative rotation of the lower shank 700 and the upper shank 800 in an opposite direction.

The extent to which the locking screw 26 is threaded into the axial bore 72 of the lower shank 700 controls the amount of compression or preload on the spring 22 which, subsequently, controls the limiting torque required to effect relative rotation of the lower shank 700 and the upper shank 800. If the locking screw 26 is threaded deeply into the lower shank 700, a higher torque will be required to disengage the teeth 82 of the lower shank 700 and the upper shank 800 than if locking screw 26 was threaded into the lower shank 700 relatively shallow.

Thus, when the driver 100 is rotated in one direction, the shaft 14 will rotate with the cylindrical body 6 and T-shaped handle until a predetermined torque is reached. When this predetermined torque is reached, a biasing force exerted by the spring 22 is overcome, allowing an inclined face 66 of the upper shank 800 to slide up a respective inclined face 66 of the lower shank 700, subsequently snapping the teeth 82 of the lower shank 700 into engagement behind a next tooth of the upper shank 800. This snapping sound is typically an audible indication to a user that a predetermined torque has been reached.

When a force beyond the required value of torque is reached, the teeth of the lower shank 700 and the upper shank 800 will continue to disengage, resulting in rotation of the handle with no further rotation of the work piece-engaging tip 12. Thus, the handle will continue to rotate, disengaging the teeth 82 with every rotational movement that will not impart continued force beyond a predefined threshold to the fastener.

When the driver 100 is rotated in the opposite direction, the T-shaped handle rotates in reverse a predetermined distance from a locked position without subsequent reverse rotation of the work piece-engaging tip 12. However, when the protrusion 85 travels the predetermined distance and locks against the opposite end of the recess 80, the driver 100 will operate as a standard driver with no torque-limiting feature since the engaging vertical face 68 will force relative rotation of the lower shank 700 and the upper shank 800 in the opposite direction without any torque-limiting feature.

The disposable torque-limiting driver of the present disclosure preferably imparts torques on the order of about 1 ounce inch to 100 inch ounces. Torques of this magnitude can be utilized in precision high torque environments such as the installation of dental, joint, vertebral implants and the like. Typically, the torque requirement is different for different operations and for different implants. Therefore, in some instances, the torques maybe around 1 inch pounds. In other instances, the predetermined torque maybe at least 30 inch pounds and yet other instances, at least 60 inch pounds, depending on an implant's specifications.

In some instances, a torque-limiting driver, such as driver 100, may be prepackaged with an implant provided for one-time use. Such an instance insures that the driver imparts the required amount of torque and has not been worn in or dulled by overuse.

In other instances, the driver 100 may be reusable. The shaft 14 may be interchangeably fixed relative to the nose cone 8 for the accommodation of multiple work piece engaging tips 12. It is also to be appreciated that the handle of the driver is not limited to a T-shape and may be provided in any other suitable configuration.

Referring to FIGS. 10-13, there is a torque-limiting driver 200. The torque-limiting driver 200 generally includes a handle. The handle 2 includes arms 4 at one end an axially extending generally hollow cylindrical body 6, a cap 2 that covers the same end of the T-shaped handle and a cylindrical end 18 opposite the T-shaped handle on the cylindrical body 6. The cap 2 may be snap-fitted to the cylindrical body 6, or may be welded, or attached by any equivalent thereof and the body is preferably molded from a plastic or other economical equivalents.

Figure 14:
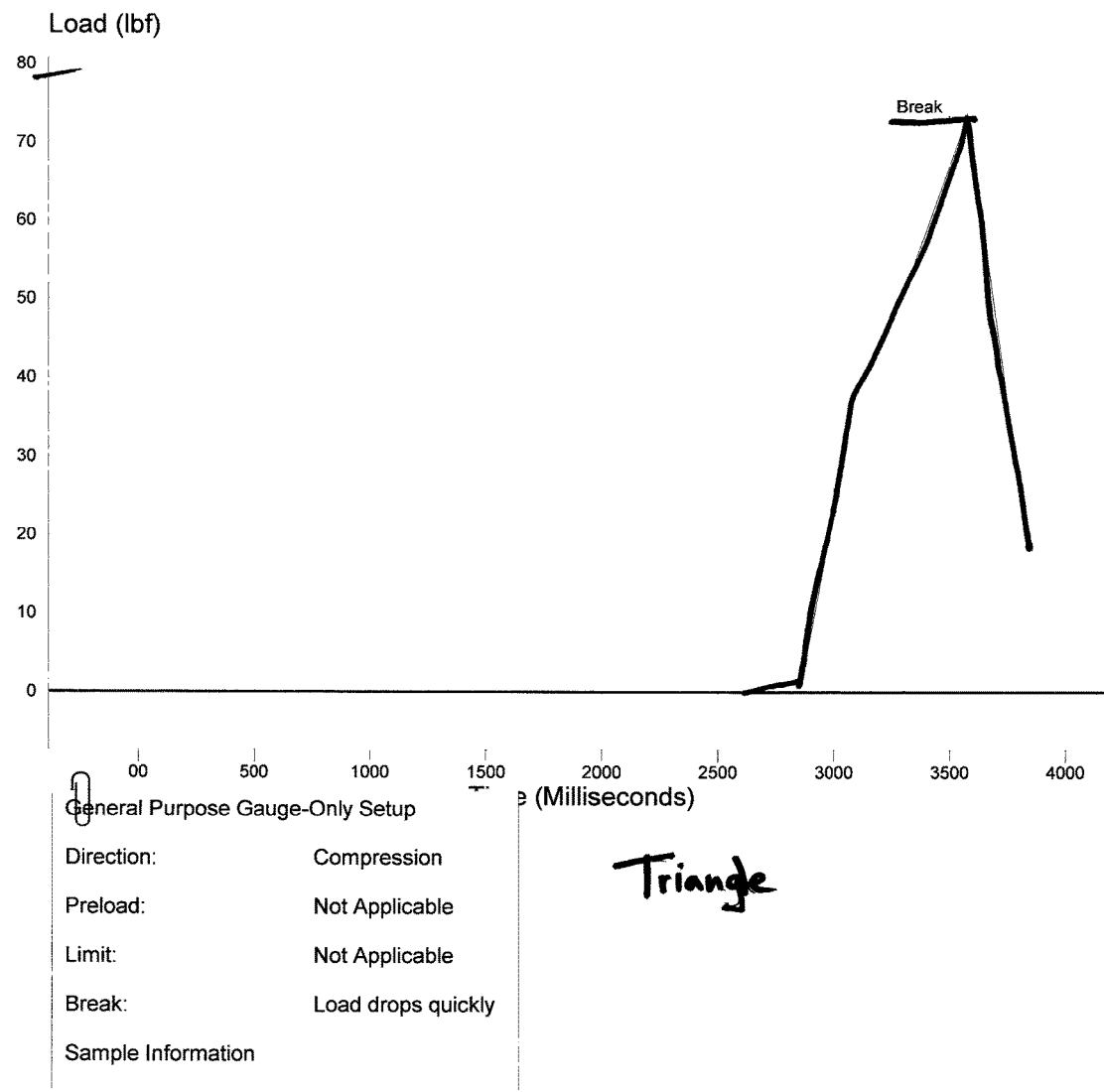
FIG. 14 shows test results with a driver having a triangular geometry.
Figure 15:
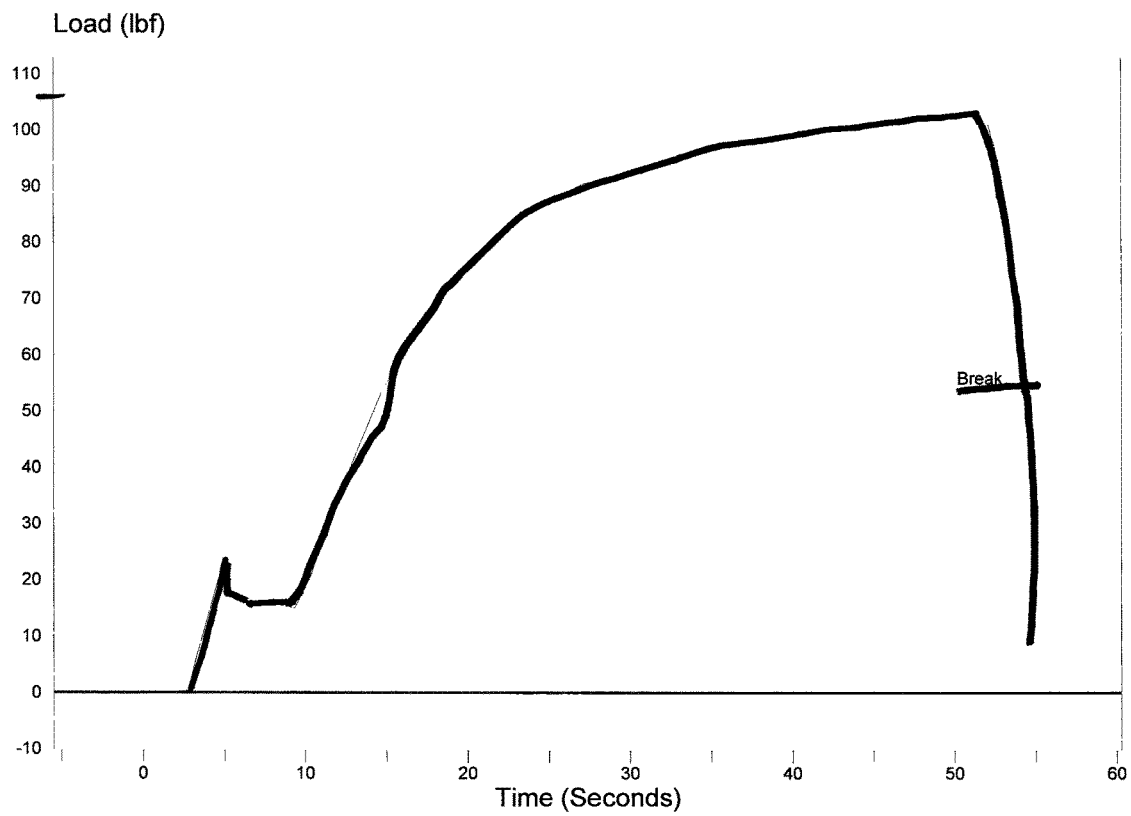
FIG. 15 shows test results with a driver having a hex geometry.
Figure 16:
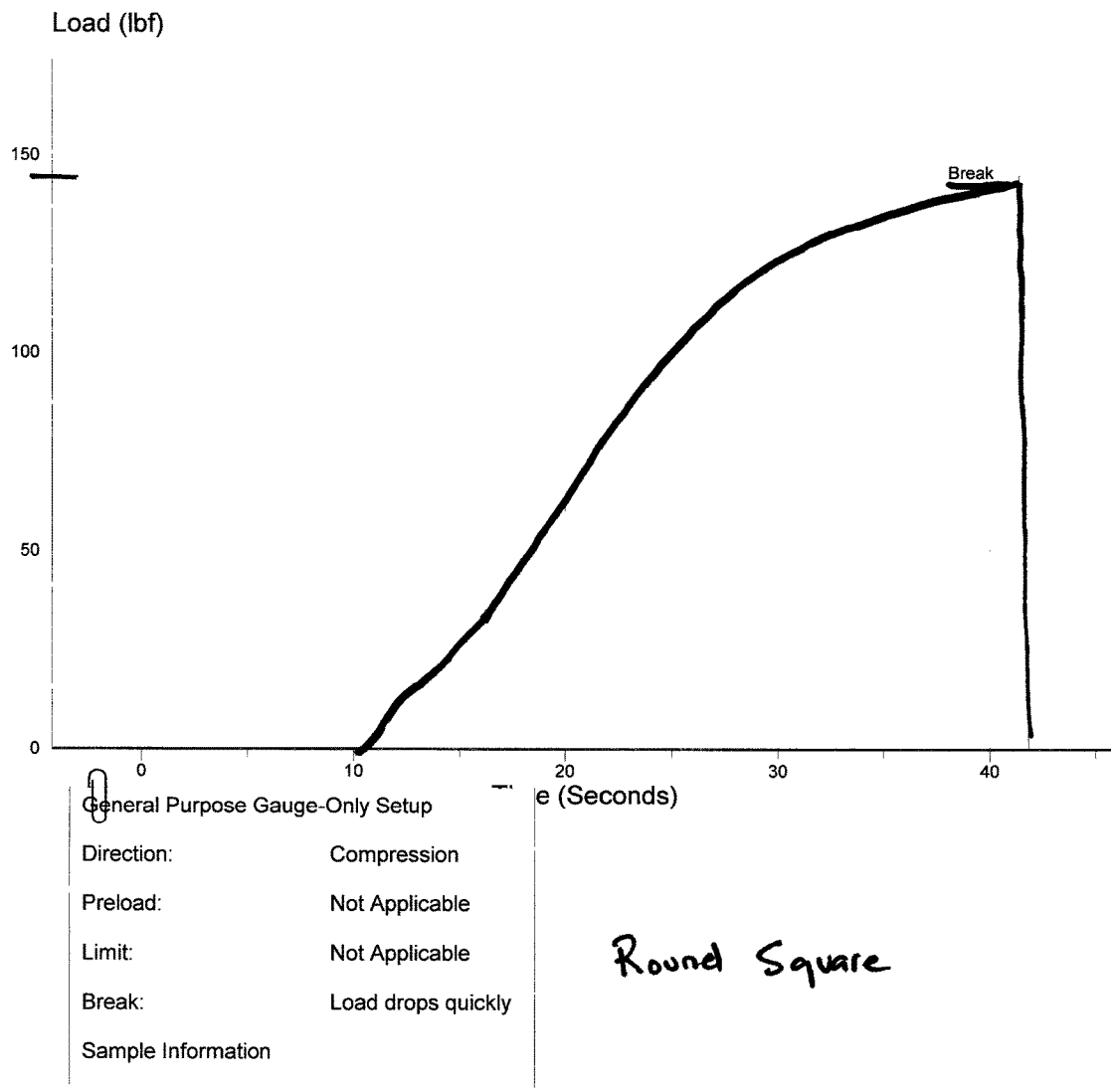
FIG. 16 shows test results with a driver having a round square geometry.

At the cylindrical end 18, there is a lower shank 700 that has and annularly tapering body and a nose cone 8 along its length. The lower shank 700 may have a plurality of support flanges 10 that add strength while saving material. At one end, the lower shank 700 tapers to an axial drive socket 9' at the end of the nose cone 8 molded of a non-metal material such as a plastic, polymer, resin including but not limited to (plastics, resins, polymers, imides, fluoropolymers, thermoplastic polymers, thermosetting plastics, and the like as well as blends or mixtures thereof) to engage a shaft 14. The shaft 14 drive connection 16' is rounded square in transverse cross-sectional shape (see FIGS. 11 and 12) and is provided, at one end, with a work piece-engaging tip 12. The shaft 14 is substantially round in cross section. The drive connection 16' is generally square but has rounded corners 95 connecting substantially flat sides 97. Testing has demonstrated that eliminating hard corners between the walls of the square cross section drive connection 16' to the drive socket 9' of lower shank 700 more evenly distributes the force applied thereto and substantially reduces, deformation, bending, breaking, and/or cracking of the non-metal nose cone 8 region of the drive socket 9' at high load (lbf) and/or inch pounds over time as compared to other geometries of drive socket and drive connection as shown in FIGS. 14-16.

In some implementations the round square implementation provides a range of use over predetermined cycles of up to almost 150 inch pounds. In some implementations the round square implementation provides a range of use over predetermined cycles of between at least about 10 and about 140 inch pounds. In addition testing has shown that the round square cross section of the drive connection 16' and drive socket 9' have a more robust connection, compared to, triangle or hexagonal and does not "strip", deform or spin in the drive socket as readily as shafts and drive sockets with hexagonal or triangular cross sections. Within the corresponding drive socket 9', as shown in FIG. 13 the radii of about 0.156 inches of the catches 99 correspond to the rounded corners 95 of the drive connection 16'. Within the drive socket 9' of the nose 8 is generally square but has rounded corners 95 connecting substantially flat sides 97. The drive socket 9' in cross section has four substantially planar walls; four arched corners (the catches 99) and each catch 99 with a preselected radius to distribute the load caused by turning shaft 14 at a predetermined torque over a predetermined number of rotations without cracking the plastic nose cone 8 material that surrounds the drive socket to a point of failure. The optimal range of radii to achieve even (as in even load) repetitive rotations can be selected to correspond to the torque requirements of a particular driver. In some implementations the optimal radii is between about 0.1482 and about 0.1638 inches. In some implementations the optimal radii is between about 0.1292304 and about 0.1716 inches. In some implementations the optimal radii is between about 0.1266 and about 0.1794 inches.

At an opposite end, the lower shank 700 has a plurality of teeth arranged in a crown gear formation, a circumferential rim 31 extending radially outwardly and an internally threaded fastener bore.

Figure 10:
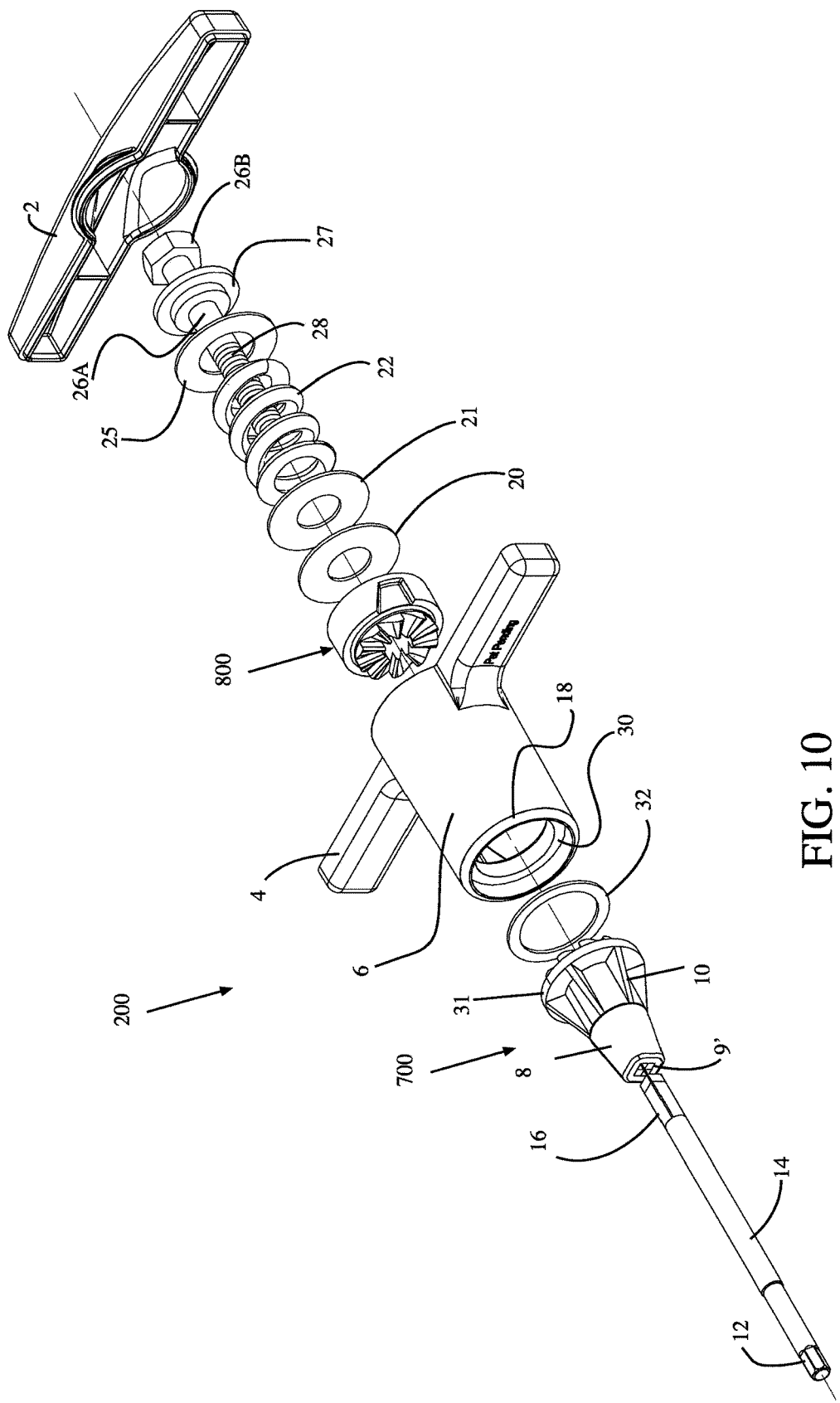
FIG. 10 is an exploded view of a driver in accordance with the present disclosure.

FIG. 10 is an exploded view of the driver 200. Inside the cylindrical body 6 a clutch assembly is disposed. The clutch assembly includes an upper shank 800 for forcibly engaging the lower shank 700. The upper shank 800 has a bottom face that has teeth arranged in a crown gear formation and an annular flange or circumferential rim extending radially outwardly.

According to aspects of one or more exemplary implementations, force is applied across lower shank 700 and upper shank 800 via spring 22 within cylindrical body 6. Inside cylindrical body 6, shown in FIG. 10 washer 20 and washer 21 are provided between upper shank 800 and spring 22. Washer 20 and washer 21 transfer pressure from spring 22 over the top face of upper shank 800. At an end of spring 22 opposite upper shank 800, shoulder washer 25 and a fastener 26A fastener head 26B hold spring 22 in a relatively compressed state. Washer between shoulder washer 25 and spring 22 to facilitate relative rotation of fastener head 26 and spring 22. The fastener is threaded 28 and said threads engage with the internally threaded fastener bore inside of the lower shank 700.

Figure 17:
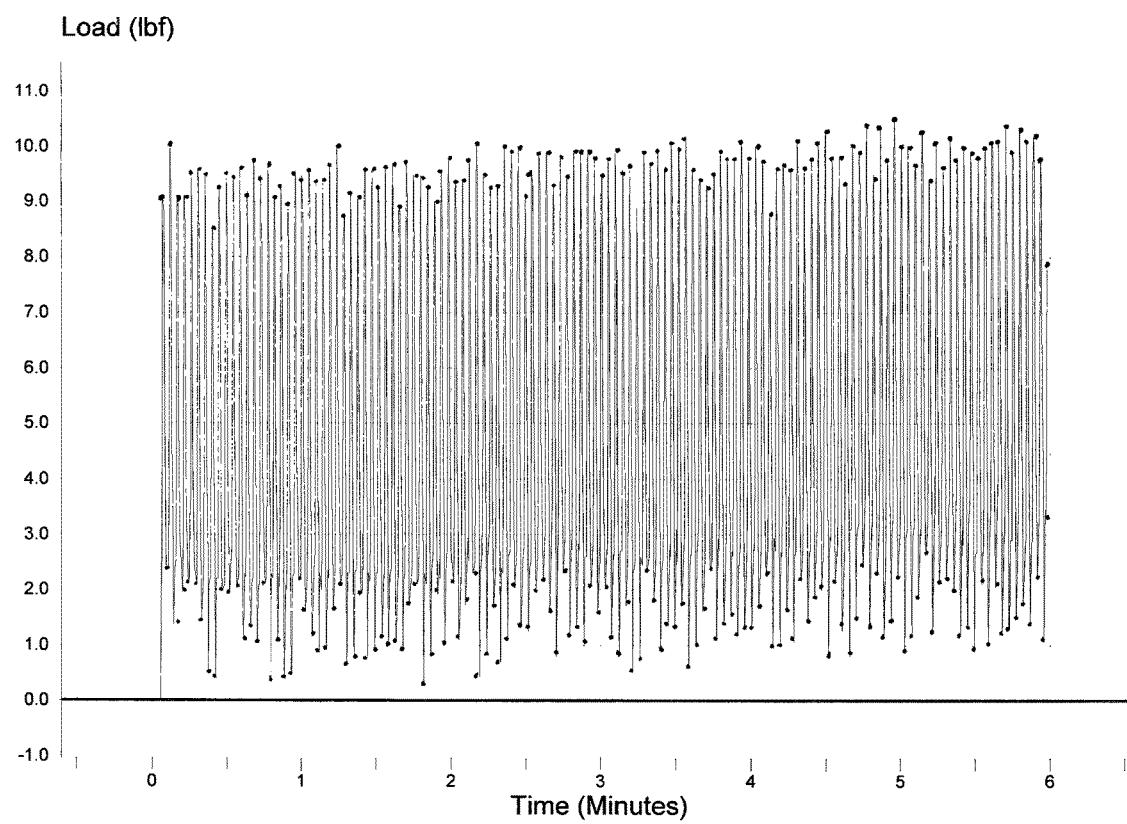
FIG. 17 shows test results of round square configurations with about 13 revolutions using a single washer.
Figure 18:
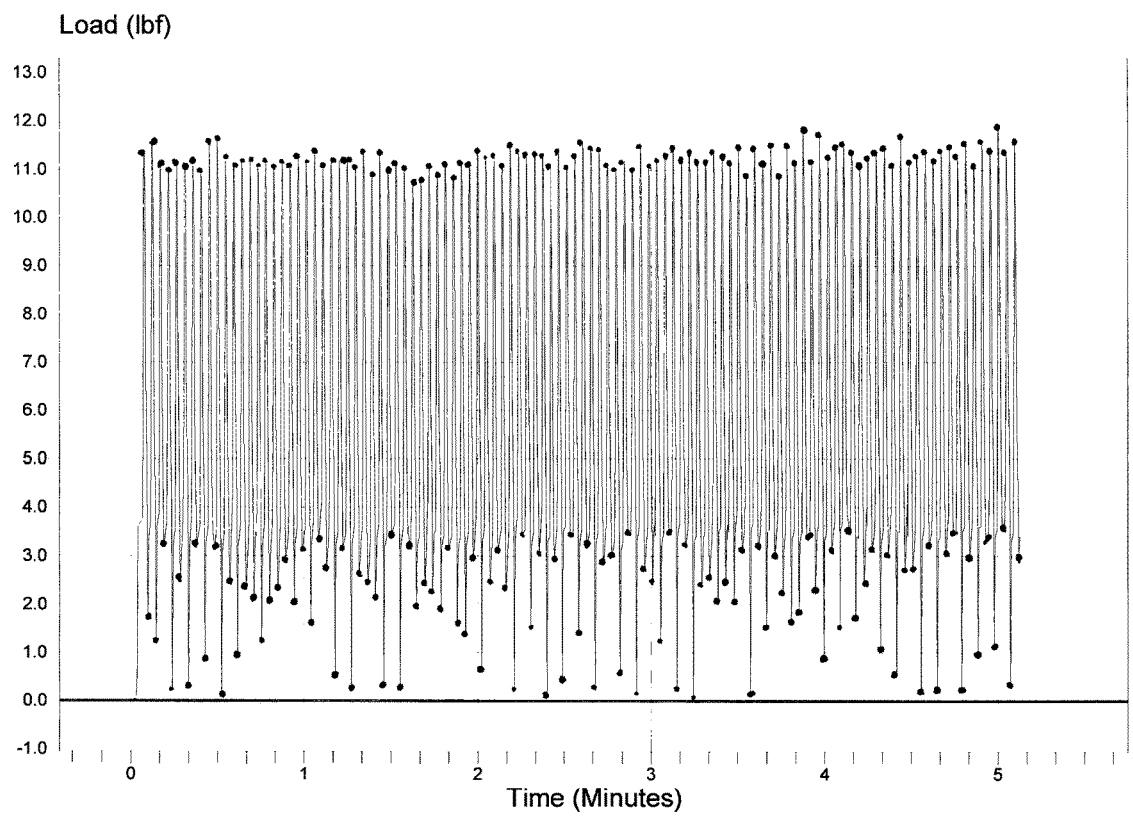
FIG. 18 shows test results of round square configurations with about 11 revolutions using two adjacent washers.

According to aspects of one or more exemplary implementations, driver 200 capable of transferring higher torque may be provided with spring 22 having a greater spring constant (i.e., force constant) or otherwise be calibrated with spring 22 exerting greater forces in an initial (rest) state. A more robust spring 22 may be used when adding washer 20 and washer 21 at the end of said spring nearest said upper shank 800, in such instance although spring 22 may have a tendency to grip relative to washer 21 the bearing surface between washer 20 and washer 21 provides for smooth rotation. FIGS. 17-18 provide test results showing that an increased load may be achieved when using a multi-washer (21 and 20) system as opposed to a single washer (20 or 21). In some implementations disclosed is a drive socket 9' which in cross section has four substantially planar walls; four arched corners (the catches 99) and each catch 99 with a preselected radius to distribute the load caused by turning shaft 14 at a predetermined torque over a predetermined number of rotations without cracking or otherwise damaging the non-metal nose cone 8 material that surrounds the drive socket to a point of failure. A more robust spring 22 increases the probability of a friction grip relative to washer 21. Provision of additional washer 20 preserves at least one free-spinning structure between the distal end of the spring 22 and upper shank 800. At the proximal end of the spring the shoulder washer 27 and washer 25 replace the cup washer 24. testing shows that a cup washer, such as that shown in FIGS. 2 and 3 may over time deform, indent, bend, break fail or partially fail from use and the pressure excreted thereon by the fastener head 26B against the cup washer 24. The shoulder washer 27 fastener head 26B interaction reduce such failure or deformation.

In assembly, drive connection 16' of shaft 14 is received into drive socket 9' of lower shank 700. Washer 32 maybe provided between circumferential rim 31 of lower shank 700 and circumferential flange 30 extending radially inward within the hollow of cylindrical body 6. Washer 32 may be of a polymer or other material having low coefficient of friction. Alternatively, circumferential rim 31 of lower shank 700 may be provided flush against circumferential flange 30 of cylindrical body 6.

While the method and agent have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

It should also be understood that a variety of changes may be made without departing from the essence of the disclosure. Such changes are also implicitly included in the description. They still fall within the scope of this disclosure. It should be understood that this disclosure is intended to yield a patent covering numerous aspects of the disclosure both independently and as an overall system and in both method and apparatus modes.

Further, each of the various elements of the disclosure and claims may also be achieved in a variety of manners. This disclosure should be understood to encompass each such variation, be it a variation of an implementation of any apparatus implementation, a method or process implementation, or even merely a variation of any element of these.

Particularly, it should be understood that as the disclosure relates to elements of the disclosure, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this disclosure is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these disclosure(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

The invention claimed is:

1. A method of reducing plastic nose cone breakage of a disposable torque-limiting driver operating at a selected torque, the method comprising:
    applying a preselected amount of torque to a tool fitted to a torque limiting device via a drive socket of a plastic nose section;
    said drive socket having been formed of four substantially planar walls and interposed between each wall is an arched corner catch each with a radius configured to distribute the force caused by turning a shaft at the predetermined torque without cracking the plastic nose cone over a predetermined number of rotations;
    wherein the predetermined torque is at least 60 inch pounds;
    wherein the nose cone continues to function within the predetermined torque range for at least about 105 cycles; and
    wherein the radius is between 0.1266 inches and 0.1794 inches.

2. The method of claim 1 wherein the predetermined torque is between about 75 inch pounds and about 85 inch pounds.

3. The method of claim 2 wherein the nose cone continues to function within the predetermined torque range for at least about 108 cycles.

4. The method of claim 2 wherein the nose cone continues to function within the predetermined torque range for at least about 138 cycles.

5. The method of claim 1 the predetermined torque is between about 105 inch pounds and about 110 inch pounds.

6. The method of claim 5 wherein the nose cone continues to function within the predetermined torque range for at least about 135 cycles.

7. The method of claim 1 the predetermined torque is above about 120 inch pounds.

8. The method of claim 7 wherein the nose cone continues to function within the predetermined torque range for at least about 135 cycles.

9. The method of claim 1, wherein the radius is between 0.1482 inches and 0.1638 inches.

10. The method of claim 1, wherein the radius is between 0.1292304 inches and 0.1716 inches.

* * * * *